United States Patent [19]

Shringarpurey et al.

[11] 4,129,509

[45] Dec. 12, 1978

[54] METALWORKING FLUID COMPOSITIONS AND METHODS OF STABILIZING SAME

[75] Inventors: Sudhir K. Shringarpurey, Cincinnati; Gerald L. Maurer, Fairfield, both of Ohio

[73] Assignee: National Research Laboratories, Cincinnati, Ohio

[21] Appl. No.: 719,813

[22] Filed: Sep. 1, 1976

Related U.S. Application Data

[63] Continuation-in-part of Ser. No. 597,756, Jul. 21, 1975, Pat. No. 4,055,655.

[51] Int. Cl.$^2$ .......................... C10M 1/04; C10M 3/04
[52] U.S. Cl. ...................................... 252/49.5; 252/36; 252/49.7; 72/42
[58] Field of Search .................. 252/49.5, 49.7, 36; 72/42

[56] References Cited

U.S. PATENT DOCUMENTS

| 2,744,870 | 5/1956 | Stillebroer et al. | 252/49.5 |
| 3,240,701 | 3/1966 | Furia | 252/49.5 |
| 3,244,630 | 4/1966 | Sheikh | 252/49.5 |
| 3,365,397 | 1/1968 | Kolarik | 252/49.7 |

OTHER PUBLICATIONS

*Chemical Abstracts*, vol. 75, No. 5, Aug. 2, 1971, p. 164, abstract No. 31794q, Avakyan, Z. et al., "Comparative Toxicity of Free Ions and Copper Complexes with Organic Acids".

Bobtelsky, M. et al., "The Metallic Complexes of Tartrates and Citrates...", in J. Amer. Chem. Soc., vol. 67, pp. 1824–1831, Oct. 1945.

*Primary Examiner*—Benjamin R. Padgett
*Assistant Examiner*—Deborah L. Kyle
*Attorney, Agent, or Firm*—Wood, Herron & Evans

[57] ABSTRACT

Stabilized metalworking fluid compositions are disclosed comprising an oil and water dispersion and, as a stabilizer therefor, a metal complex of a metal ion and a polyfunctional organic ligand. The metal complexes have an aqueous proton induced dissociation property represented by a sigmoidally-shaped curve on a cartesian coordinate plot of the negative log of the metal ion concentration versus the negative log of hydrogen ion concentration. This dissociation property causes a controlled release of metal ion into the oil and water dispersion to impart metal working stability to the dispersion. Metal working emulsions of oil and water are stabilized by the addition thereto of minor amounts of a metal complex, e.g., disodium monocopper(II) citrate, which at alkaline pH metalworking conditions above about 7 to about 9 releases metal cations to the emulsions imparting stabilizing characteristics which prevent emulsion degradation by a number of factors commonly encountered in metalworking operations. The stabilized compositions of this invention have greatly improved service life and offer significant economies in metalworking operations.

24 Claims, 10 Drawing Figures

METALWORKING FLUID COMPOSITIONS AND METHODS OF STABILIZING SAME

RELATED APPLICATIONS

Figure 1:
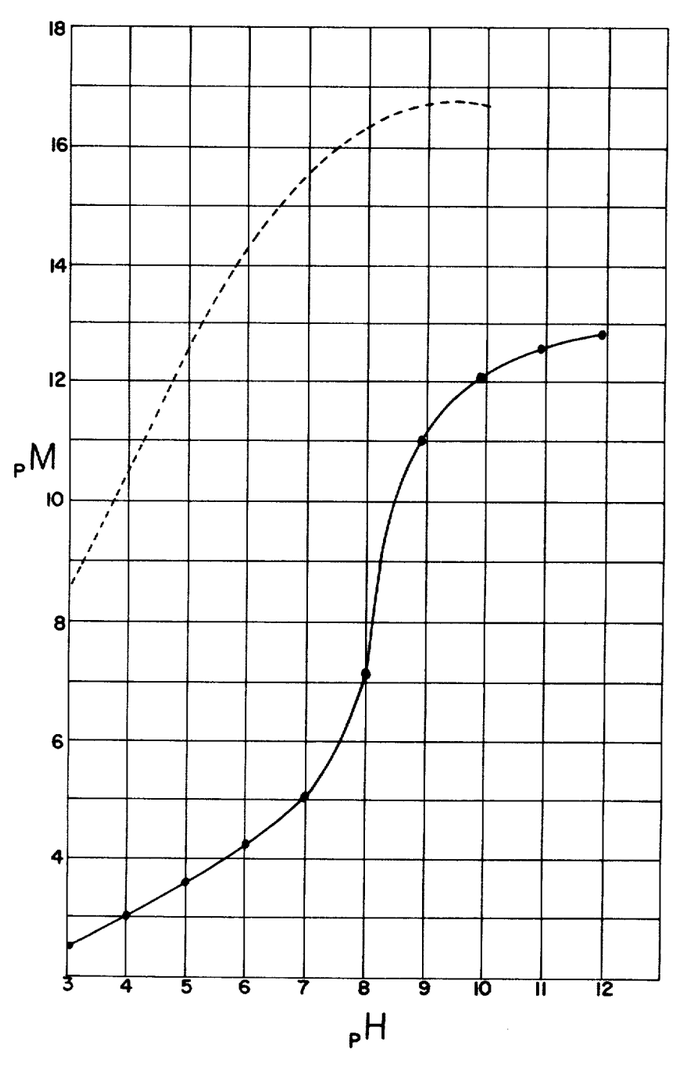

This application is a continuation-in-part of application Ser. No. 597,756 filed July 21, 1975 by Sudhir K. Shringarpurey and Gerald L. Maurer now U.S. Pat. No. 4,055,655.

BACKGROUND OF THE INVENTION

Metalworking fluid compositions are well known in the art which function to lubricate and cool various metallic surfaces during metalworking operations such as cutting, turning, drilling, grinding, quenching and the like. In the past, metalworking compositions have not exhibited an extensive service life. For example, in use the oil and water emulsions or dispersions usually deteriorate or even physically breakdown within a limited period of time even as short as a few weeks. The deterioration of the emulsions has been attributed to a number of causes present in metalworking operations including the introduction of foreign matter such as grit or dirt, metal particles, polyvalent metallic ions, bacteria, metalworking conditions including pressure and temperature, etc., among other factors.

The lack of extensive stability, therefore, in metalworking compositions has imposed serious direct and indirect disadvantages involving their use in metalworking operations. For example, the short term life of metalworkfing fluids increases the labor and material costs associated with the handling and utilization of the fluids in metalworking systems. Furthermore, the deterioration of such fluids increases wear on the metalworking machines themselves and decreases tool life due to loss of performance of the metalworking fluids. Among other ancillary effects of metalworking fluid deterioration are increased rejection of work pieces, decreased production and increased costs associated with downtime, expensive disposal of discarded fluids, worker health problems associated with their use, and environmental pollution. Therefore, metalworking compositions having extended service life and stabilized against deterioration due to metalworking conditions, among other desirable properties, are very important not only to industry wherein they are used, but also to the environment within which we live.

Various prior art approaches have been taken toward the improvement of metalworking compositions and in an effort to overcome or minimize direct and indirect disadvantages involved in the use of such metalworking fluids. Representative of prior art patents in this area are U.S. Pat. Nos. 2,688,146; 3,240,701; 3,244,630 and 3,365,397. Such patents and the efforts of others in substance have been directed to overcoming the factors contributing to emulsion deterioration and breakdown. Suffice it say that the results of such efforts have been less than satisfactory and there has been a need for improved metalworking compositions which would provide new results; and overcome the present problems and disadvantages.

SUMMARY OF THE INVENTION

As disclosed in our earlier application above mentioned, the antimicrobial activity of certain metal complexes, e.g., the dialkali monocopper (II) citrates has been established by their toxic and growth-inhibiting action against a number of microbes in a media of oil emulsions employed as coolants in various machining operations. The efficacy of the metal complexes in industrial coolant liquids was established as disclosed where numbers of microbes were found to proliferate. As also disclosed in our earlier application, it was significantly found that at alkaline pH's of metalworking conditions the metal complexes were remarkably effective.

This application is directed to metalworking fluid compositions and methods of stabilizing same; and amplifies further our discoveries with respect thereto. According to this invention, metalworking emulsions, i.e., oil and water dispersions, are stabilized by the addition of an effective stabilizing amount of a metal complex of a metal ion and a polyfunctional organic ligand. These metal complexes were disclosed in our earlier application. The stabilizing metal complex is characterized by a very unexpected aqueous proton induced dissociation property which causes the controlled release of metal ion into the oil and water dispersions to impart metalworking stability to the dispersions. This dissociation property is represented by a sigmoidally-shaped curve on a cartesian coordinate plot of the negative log of the metal ion concentration versus the negative log of hydrogen ion concentration, i.e., a pM-pH diagram. Quite unexpectedly, it has been discovered that metalworking fluids can be stabilized against attack and deterioration by different causes. Thus, in one aspect of our invention, metalworking fluids have been stabilized against deterioration by a general purpose metal complex stabilizer additive. For instance, as disclosed in our earlier application, certain metal complexes are effective as antimicrobial agents in metalworking emulsions,. It has been further developed that these metal complexes impart other stabilizing characteristics to the metalworking fluids and achieve improvements and advantages heretofore unobtained to applicants' knowledge in metalworking fluids. This stability is not only achieved against bacteria, but the fluids are stabilized against degradation by physical, chemical, and physicochemical causes associated with metalworking conditions including heat, pressure, metalworking compositional environment of metalworking particles, polyvalent ions, etc. The stability of metalworking fluids has, according to this invention, been proved dramatic. For example, in industrial coolant areas, service life of fluids has been extended from a period of for example a few weeks to nearly a year or more, and present results indicate that service life may be extended even indefinitely. The metal complex stabilizers themselves are very stable at relatively high alkaline pH's on the order of about 9 or 10 to about 12. However, in an alkaline pH range above 7 to about 9 where metalworking fluids are required to function, the stabilizing complexes very advantageously impart stabilizing effects to the metalworking fluids. It has also been discovered in this connection that metalworking compositions may be provided with a stabilizing metal complex in very minor amounts, i.e., amounts of which may be below those amounts which would exhibit biocidal activity, yet still such metalworking fluids may be stabilized against degradation by all factors in the metalworking environment.

Thus, the compositions and methods of this invention are directed to imparting stability to otherwise degradable oil and water dispersions which are subject to deterioration by a number of causes. For example, biostability can be imparted to metalworking fluids by the introduction of the metal complexes, even in amounts less than biocidal amounts. On the other hand, general emulsion stability can be achieved by the introduction of amounts of the metal complex to stabilize the emulsions against degradation by extraneous sources such as metal particles, polyvalent metal ions and the like. Furthermore, metalworking fluids may be imparted with extreme pressure and heat resistant properties by employing the stabilizers according to this invention. In another of its aspects, the compositions of this invention reduce chemical interaction of other moieties with the emulsified particles which would otherwise tend to diminish stability. These and other advantages of stabilizing effectiveness are achieved according to the principles of this invention as will be understood in view of this description.

The theories of underlying reasons for the rather unexpected activities of the metal complex stabilizers according to this invention have been explored. While applicants do not wish to be limited to theoretical reasoning, it is believed it may be helpful to a further understanding of the attributes and unexpected results achieved according to this invention. It is presently believed, in the case of oil and water dispersions (whether they be oil-in-water or water-in-oil), that such dispersions may be either biodegradable, chemically degradable by reason of chemical species in the fluid media, and physically degradable by conditions such as mechanical forces, or combinations of any two or more of such factors. As it is known, such oil and water dispersions contain emulsifying agents and these emulsifying agents are typically of the "anionic" and/or "non-ionic" type. The emulsifying agents by reason of their hydrophilic-hydrophobic natures enable the suspension of the oil particles within a continuous phase of the fluid. Such electronegative species, for example carboxyl and sulfonate groups of the emulsifying agent, impart electronegative surface charges to the oil droplet. The combined electronegativity of such an emulsified particle is generally referred to as the Zeta potential. In substance, the Zeta potential is related to the force and distance over which the emulsified particles can repel each other and thus prevent flocculation. This of course is an oversimplification of such oil and water dispersions. Nevertheless, one perhaps might have expected that the introduction of a highly charged divalent metal cation or a similar species of the stabilizing metal complexes would interfere with the emulsion stability and cause perhaps flocculation by reason of neutralization of the highly electronegative character of the emulsion droplets.

Thus, in a broader aspect, this invention provides a method for stabilizing oil and water dispersions, and stabilized compositions, by the addition thereto of a multivalent metal ion which forms a coordinate bond with the electronegative emulsifying agent. The stabilizing effects of such a coordinate formation are realized because the electronegativity still exists to prevent demulsification and, moreover, the other susceptible sites of the emulsifying agent are now blocked against enzymatic degradation and to permit the metal ion to be conveyed as a boundary lubricant to the tool-workpiece interface. This method is attributed to the highly electronegative character of the emulsified droplet either initiating or contributing to the dissociation of the metal complex and allowing the coordination of the metal cation with the electronegative entities of the emulsified droplets, for example, the carboxyl, sulfonate, or alcoholic hydroxyl moieties of the emulsifying agents. This blocking of these biosusceptible or functional groups prevents the enzymatic degradation of these structures, which enzymatic degradation is common to and associated with the microbial metabolism. However, it is quite unexpected that the introduction of the metallic complexes or the introduction of such metal ions has been found not to cause demulsification of the electronegatively charged emulsion droplets. This is so because the amount of positively charged ions associated with the electronegative surface of the oil droplet, while sufficient to impart biostability, is not sufficient to decrease the electronegativity of the particle to the point of demulsification. Therefore, the effect of forming coordinate structures with emulsifying agents is, we believe, a new method in the stabilization of emulsions.

It has also been found that the introduction of the metal complex stabilizers of this invention contribute to extreme heat and pressure-resistant properties of the emulsion under metalworking procedures. Such extreme heat and pressure resistant properties are afforded by the coordinate structure of metal ions and emulsifying agents in the stabilized metalworking compositions of this invention. These properties are exhibited by the metal cation or the metal complex being transported to and subsequently associated with the electronegative species of the emulsified droplets as above mentioned. The emulsified droplets are continuously brought into intimate contact with the toolworkpiece interface found in metal working procedures. For example, under the heat and pressure of the metal working process, the copper associated with the emulsified droplets at the interface, enters into an oxidation-reduction process serving to lubricate the metal surfaces yet without degradation of the emulsion to an unusable state. Furthermore, in actual practice, probably due to the generation of highly reactive cations at the tool-workpiece interface in any machining operation involving metallic substrates, the metal working fluid becomes loaded with metallic ions which, by displacement, tend to replace the cations contained in the metal complex and further allow them to migrate and associate with electronegative structures of the emulsified particle, in effect, coating it with cation.

While the chemical nature of the metal complex stabilizer is such that it is highly soluble in aqueous systems, due to its unique proton dissociation property at the pH of the metalworking conditions, it readily dissociates such that the metal cation becomes transported to the oil phase of the emulsion from the aqueous phase. This surprising phenomenon has been demonstrated by two phase extraction of the oil and water emulsion system treated with the metal complex at concentrations which are even well below those found to be biocidal in nature. More specifically, emulsions treated with disodium monocupric citrate in a concentration providing about 50 to about 100 mg $Cu^{++}$ per liter of emulsion, for example 1/10 – 1/5 of the biocidal dosage in a particular medium, have been studied. Examination of the mixture of metal complex agent and emulsions by two-phase extraction employing chloroform or other chlorinated hydrocarbons reveals that the copper is present in the organic phase. While the exact mechanism of this reaction has not been specifically elucidated, nevertheless the biostability, chemical stability and physicochemical stabilities imparted by virtue of the treatment of emulsions with the metal complexes of this invention have been empirically observed. Furthermore, biostability imparted by virtue of less than biocidal or biostatic amounts of metal complexes is considered remarkable and must be associated with the reaction of moieties of the organic phase rendering them nonsusceptible to bacterial attack as opposed to a direct cation reaction with microbial entities associated with the aqueous phase.

For example, it has been heretofore noted that polyvalent metal cations may be generated in the machining process, such as cations of iron, aluminum and the like. On the other hand, other such polyvalent metal cations such as calcium and magnesium may be present in the aqueous medium employed in metalworking fluids. These ions may otherwise be termed "generated ions", i.e., those produced by machining operations, or "native ions", i.e., those which are inherently present in the aqueous media of the metalworking fluid compositions. The polyvalent cations normally interfere with the metalworking processes and furthermore contribute to the instability of the emulsified particles. It has, however, been empirically determined that the stabilizers of this invention render stable the emulsions from interference by such polyvalent metal ions, i.e., those either generated by or those which are inherent in metalworking fluids. Thus the stabilizing components of the metalworking compositions of this invention tend to, upon dissociation, not only impart stability to the emulsified particles by reason of their association therewith and the inherent advantages resulting therefrom, but also inhibit unwanted polyvalent species in the media.

The metal complexes employed as stabilizers in the compositions and methods of this invention release large amounts of metal ion from their coordinate structures at a pH of about 4 to about 9 and, most preferably at a pH of between about 7 and about 9 or 10, i.e., those which are normally encountered in metalworking compositions. Upon demand, by reason of their unique dissociation property as demonstrated by sigmoidally shaped behavior on a pM-pH diagram, these agents offer controlled release of metal ions at a pH compatible with metalworking conditions. Furthermore, by reason of the organic ligand nature of the metal complexes, as pointed out above, the activity of other polyvalent metal cations or other extraneous moieties present in the metalworking fluids, which otherwise might impart either instability or which might adversely affect stability of the metalworking emulsions, is inhibited. Therefore, the metal complex stabilizers of this invention are to be differentiated from other metal complexes wherein metal cations have been complexed with organic ligands represented by ethylenediaminetetraacetic acid (EDTA), diethylenetriaminepetnaacetic acid (DTPA), other amino acids, or the like which have relatively high stability or chemical inertness and do not make the metal ion available in amounts which coordinate with the electronegative emulsifying agents to any significant degree and, therefore, cannot impart stability to the emulsion. Also, such known complexes do not offer a controlled release of metal ion or dissociation property represented by a sigmoidal pM-pH diagram. Rather, such known metal complexes by reason of their stability and chemical inertness tend to dissociate to a lesser extent in rather a linear fashion. Furthermore, this invention provides complexes which are capable of aqueous solubility in high concentrations by reason of their ionic character and yet they remain in the stable form. This property of solubility, particularly in alkaline media as in this instance, enables the production of concentrates capable of producing, upon demand, in an emulsion system, the metal ion to impart metalworking stability to the emulsion. Such a solubility property is to be distinguished from the rather insoluble metal compounds of the prior art which employ metal cation-anionic components and which are virtually insoluble in such media; or those metal complexes which, even though they may be soluble, bind the metal ion in such complex state that it is only slightly dissociated and, therefoe, scarcely available for metal ion release and coordination with the emulsified particle.

The term "metalworking fluid compositions" as used in accordance with this description and as understood in the art therefore applies to those fluids which function to lubricate, cool, clean and inhibit decomposition of metal surfaces during the process of metalworking. These fluids are well known to those who practice the art of metalworking. There are two basic areas of metalworking, i.e., mechanical operations, referring to cutting, drilling, reaming, turning, milling, broaching, grinding, etc. along with forming, bending, rolling, drawing, and the like; and non-mechanical operations referring to washing, quenching after heat-treating, and the like. It would be generally accepted that metalworking compositions in mechanical operations provide lubricity, cooling, cleaning and rust inhibiting functions, whereas in non-mechanical operations they primarily provide cleaning, rust inhibiting and cooling functions.

The oil and water dispersions which constitute the metalworking compositions containing the stabilizer in accordance with the principles of this invention may, as mentioned above, be either of the oil-in-water type or the water-in-oil type. These dispersions have mainly been referred to as oil emulsions or soluble oil compositions in the art. Such compositions are characterized essentially by two phases, i.e., a liquid-in-liquid system in which there is a dispersed phase and a continuous phase. Perhaps classically, where the particle size of the dispersed phase is on an order of magnitude greater than about 0.1 micron in particle size, they have been termed "emulsions". Where the particle size is in a colloidal range of about 1 millimicron to about 0.1 micron, the dispersion may be of a colloidal nature. Accordingly, whether one wishes to characterize them as a coarse emulsion or colloidal suspensions, the fluid compositions are essentially constituted by organic and aqueous phases, i.e., in a two-phase system consisting of one liquid in another liquid in which the first liquid is not miscible. Furthermore, the term "oil" is used herein to identify a large class of substances whether of the mineral, vegetable, animal, essential or edible origin. Those oils, however, that are employed for metalworking purposes are usually derived from the class of mineral oils, either petroleum or petroleum-derived and, particularly, from the lubricating class. These dispersions include emulsifying agents typically of the anionic or nonionic type. In the case of the anionic agents, the anion portion possesses the polar character required to bring about the desired surface active effects and it contributes an electronegativity to the suspended oil droplets or particles. In the case of the nonionic agents, an electronegativity is imparted to the oil particle by virtue of a high density of inherent electronegativity. Most commonly, the emulsifying agents employed in the metal working emulsions are anionic and/or nonionic surfactants. The anionic surfactants contain a negatively charged ion-containing portion and an oil dispersible or oleophilic portion in the surfactant molecule. The surfactant may be (1) of the group of saponified fatty acids of soaps, or (2) of saponified petroleum oil such as sodium salts or organic sulfonates or sulfates, or (3) of saponified esters, alcohols or glycols, with the latter being well known as anionic synthetic surfactants. Examples of these anionic detergents include the alkylaryl sulfonates of amine salts thereof such as sulfonates of dodecyl benzene or diethanolamine salts of dodecyl benzene sulfonic acid; the sulfates of straight chain primary alcohols, or fatty alcohols ($C_6$-$C_{24}$) which are products of the Oxo process (i.e., sodium lauryl sulfate). A saponified light petroleum oil such as sulfonated petroleum distillation residue (e.g.,mahogany oil) is common. In general, the majority of surfactants or emulsifying agents of the "anionic" type are alkali or amine salts or organic acids. Frequently, sulfonic acids are employed where the structure of the organic portion is not well known, as in the case of familiar "petroleum sulfonates". Most of these sulfonates contain many chemical species. The class name given to most of them is "alkylaryl sulfonate". Simply, this means that a paraffinic hydrocarbon is bonded to an aromatic or benzene hydrocarbon nucleus (usually benzene or naphthalene) and the aromatic portion has been sulfonated. Examples of saponified fatty acids ($C_6$-$C_{24}$) are the sodium or potassium salts of myristic, palmitic, stearic, oleic or linoleic acids or mixtures thereof. Also, in this class of anionic surfactants are alkali and alkaline earth metal salts of neutral phosphoric acid esters of oxyalkylated (oxyethylated) higher alkyl phenols or aliphatic monohydric alcohols. Examples are potassium and sodium salts of phosphate esters of isodecyl alcohol, ethylene oxide adducts. Thus, herein anionic surfactants or emulsifying agents include soaps or synthetic surfactants of the class of alkali, alkaline and amine salts of the organic sulfonates, phosphates or sulfates.

The nonionic surfactants suitable for use commonly have hydrophilic portions or side chains usually of the polyoxyalkylene type. The oil soluble or dispersible part of the molecule is derived from either fatty acids, alcohol, amides or amines. By suitable choice of the starting materials and regulation of the length of the polyoxyalkylene chain, the surfactant parts of nonionic surfactants may be varied as is well known. Suitable examples of nonionic surfactants include alkylphenoxy polyoxyethylene glycols, for example, ethylene oxide adduct of either octyl-, nonyl- or tridecyl- phenol and the like. These mentioned nonionic surfactants are usually prepared by the reaction of alkyl phenol with ethylene oxide. Other specific examples of nonionic detergents include glycerol monooleate, oleyl monoisopropanolamide, sorbitol dioleate, alkylol amides prepared by reacting alkanolamides such as monisopropanolamine, diethanolamine, or monobutanolamine with fatty acids such as oleic, pelargonic, lauric and elaidic.

The metalworking compositions typically are formulated as is well known in the art by a combination of a lubricating oil, such as a solvent-refined paraffinic or napthenic oil, an emulsifying agent of the anionic type as mentioned above, and special additives including commonly rust-proofing agents and the like. Commonly, in the industry such compositions containing the additives are termed "neat oil" and the neat oil composition is then mixed with sufficient water to provide an emulsion. The volume of water will vary depending upon the various factors and whether the emulsion is either an oil-in-water or water-in-oil emulsion. For example, the oil phase may vary over wide ranges of from about 1 to about 95 or more percent by weight with the balance being the water phase and other amounts of the emulsifying agents and additives. Usually, an emulsifying agent may be within the range of about 5 to about 50 percent by weight. In lubricating and cutting oil compositions, the neat oil composition is mixed with sufficient volume of water to provide an emulsion which contains by volume about 90 to about 99% water and 10% to 1% by volume of the oil formulation. The ingredients of the neat oil are usually about 30 to about 90% lubricating oil, about 10 to about 25% emulsifier with the balance perhaps being additives of the type mentioned above.

The stabilizing metal ion is present in the lubricating oil composition in an effective amount to provide metalworking stability. This effective amount may vary depending upon a number of factors, including the particular metal being worked, pH, contaminants, and amounts of oil and water phases, emulsifier, metalworking cations, the particular metal complex, and the like. Generally, for example, in an emulsion formed from the neat oil composition as above mentioned, the stabilizing metal ion is usually contained in terms of milligrams of metal ion per liter of oil phase in a range of about 10 to about 500 mg/liter. Where a metal complex provides the metal ion, the complex is added to the aqueous phase. After such addition, the metal ion, as explained above, migrates to form coordinate bonds with the emulsifying agent establishing an equilibrium between the oil and water phases. As the metal ion is depleted during metalworking from either phase, more complex may be added to maintain the effective stabilizing amount. More particularly, in a cutting or lubricating oil composition for iron metalworking of about 97 percent by volume water and 3 percent by volume oil as above mentioned, with about 10–15% emulsifier, and disodium monocupric citrate is employed as the stabilizing agent, 500 mg of copper per liter of aqueous phase will obtain toxic action against bacteria. However, as mentioned above, metal working stability may be imparted to the emulsion with as little as 10–100 mg/liter of the copper cation, or well below the toxicity levels. However, amounts of the metal complexing agent or ion outside of these ranges may be used.

the metalworking stabilizers of this invention may be provided to the emulsion in a number of ways. For example, the stabilizing metal complex may be added to the aqueous phase of the emulsion prior to preparation and thereafter the neat oil composition containing the oil, emulsifier and the additives may be added and thereby the emulsion is formed, perhaps with some agitation. On the other hand, the emulsion may be formed first and then the stabilizing metal complex may be added to the formed emulsion. The emulsion is formed so as not to decompose the metal complexing agent. Specifically, in the case of metal complexes of zinc, nickel and copper citrate, these are relatively stable under alkaline conditions up to about a pH of 12, but yet impart the desired stabilizing effect to metalworking emulsions at an alkaline pH of up to about 9 or 10. Thus, the pH is adjusted on the alkaline side from about 7 to about 10 in the fluid compositions in order that the metal complex is not first decomposed and so a pH of in about the mid range of about 8.5 is achieved.

In a presently preferred form, the stabilizing agent of this invention comprises a monometal complex of a multivalent metal and a polyfunctional organic ligand in a ratio of 1:1 of the metal to the ligand, the complex having a dissociation property represented by a sigmoidally shaped plot on a pM-pH diagram. A specific example of the metal complex is dialkali monocopper-(II) citrate represented by disodium-, dipotassium- or dilithium- monocopper(II) citrate. These dialkali monocopper(II) citrates have a dissociation property represented by a sigmoidal plot wherein the curve of two directions meets at a point within the pH range of about 7 to about 9. It has been established that these monocopper(II) complexes in basic media, on the order of about 9 to about 12, are very stable, i.e., having an effective stability constant, $K_{eff}$ on the order of about $10^{12}$ to about $10^{13}$. However, $K_{eff}$ of these monocopper(II) citrate complexes at a pH of about 7–8 in on the order of about $10^5$ to about $10^8$. Therefore, at or about a pH around 7–8, the effective stability constant of the monocopper(II) citrate complex is considerably lower (a thousand to several hundreds of thousand times lower) and a significant free $Cu^{++}$ concentration is available for stabilizing activity. For example, about 10% of the copper in the complex is in the ionized state at or about pH 7 while approximately 0.1% of the copper is ionized at or about pH 9. This would not be true for an EDTA or polyamine complex of a multivalent metal such as copper, since its stability constant ($10^{14}$ to $10^{16}$) will vary only slightly in the normal pH of 7 to 9. Such EDTA complexes do exhibit a pH effect on the stability constant, but it is represented by a smooth, monotonic curve reaching a limiting effect by proton induced dissociation at pH values from about 7 to about 9, yielding only from about 0.001% ionized species at or about pH 7 to as little as 0.00001% ionized species at or about pH 9. It is to be understood that the stabilizing complexes will operate over a pH range of about 3 to about 12. Above about pH 12, the complexes tend to be destroyed by the alkaline media, precipitating from the media as hydrous metal oxides. Below about pH 6, i.e., about 3 to about 6, the instability of the metal complex results in a high concentration of the free $Cu^{++}$ in solution which will effect biostability and other stabilizing functions as above mentioned. In the mid range of about 7 to about 9, the controlled release is most effective. Thus, these complexes provide controlled release of metal ion between about 10% to about 0.1% of a complexed metal in the pH range of about 7 to 9, which metal ion is then available for coordination and stabilizing functions.

In accordance with this description and the presently preferred embodiment, it will become apparent that other stabilizing metal complexes of polyfunctional organic ligands respond to the model of this invention where they exhibit the dissociation property characterized by a sigmoid curve on a standard pM-pH diagram. For example, based upon the monometalpolyfunctional organic ligand complex of this invention as a stabilizing agent, other metal ions of a multivalent nature, specifically divalent and polyvalent cations including zinc, nickel, chromium, bismuth, mercury, silver, cobalt, and other similar metallic or heavy metal cations may be employed. The complexes of heavier metals are considered more toxic than those of the lighter metals. Other polyfunctional organic ligands may be substituted for the citric acid specifically exemplified by the preferred embodiment of this invention. Included among other polyfunctional ligands are the broader class of alpha or beta hydroxy polycarboxylic acids into which class the citric acid falls. Also, other functionally substituted acids such as alpha or beta amino, sulfhydro, phosphinol, etc., can be substituted in the molecular model of the metal complexes of this invention and similar results can be achieved. In general from a metal complex formula standpoint, the monometal complex of copper and citric acid corresponds to a complex formula exhibited by either of the following structural forms (A) and (B).

The (A) form is believed to be the preferred form by applying free energy considerations. A single proton introduced into the complex structure represented by either form (A) or (B) prevents the formation of stable 5- or 6- member coordinate rings. With the introduction of a proton, only 7- member rings may be formed by the coordination of the acetate electron donors and such 7-member ring structures are unstable. Therefore, the complex molecule dissociates and presents the metal ion for its toxic or stabilizing effects. In comparison, metal complexes of EDTA or other polyamines require four or more protons, and hence greater acidity, to dissociate the complex; this accounts for the small pH effect exhibited by such complexes in a pM-pH diagram.

The (A) and (B) structural forms may be more generally represented by the following models:

In the above models, the solid line segments represent a chemical bond between elements in the skeletal structure of the molecule: X, Y and Z represent electron pair donors; (R) represents any elemental or molecular species or group; M represents a metal and wherein the proton affinity of X is greater than that of Z, Y or R. It will therefore be appreciated that other Lewis base proton pairs, and other metal ions, may be substituted into these structural models for oxygen, divalent copper, or, for that matter, the carbon atoms to provide a molecular model which will similarly dissociate upon the introduction of one proton or similarly behaving species as exhibited by the sigmodial behavior on a pM-pH diagram. The molecular models are thus alternative expressions for the stabilizing agents of this invention.

The invention and its various embodiments and advantages will be further understood with reference to the following examples, detailed descriptions and the drawing which illustrate the preparation of stabilizing complexes, and stabilized metalworking fluids.

PREPARATION OF STABILIZING COMPLEXES

A. Dilithium monocopper(II) citrate 10 millimoles of lithium citrate were dissolved in 10 milliliters of water. To this solution, 10 millimoles of cupric chloride ($CuCl_2.2H_2O$) were added gradually with stirring. A deep blue solution was formed. This was neutralized to a pH of about 7 with 10 millimoles of lithium hydroxide ($LiOH.H_2O$). This solution, when evaporated to dryness, gave a deep blue, semicrystalline solid. This solid was ground to a fine powder and the lithium chloride was extracted with 50 milliliters of dry methanol, five times, at 35° C. The blue solid which remained behind was evacuated to remove methanol and desiccated. An attempt was made to crystallize the salt from water-organic solvent systems, but apparently due to the extremely hygroscopic nature of the salt and the high negative charge on the ionized molecule, the solid obtained was microcrystalline to amorphous. The following formula is proposed for the 1:1 complex of copper and citrate based on elucidation of the structure and analyses described hereinafter.

$$Li_2CuC_6H_4O_7.XH_2O$$

Depending upon the degree of hydration, the following formula weights (F.W.) and corresponding percentages of copper content are proposed:

$$Li_2CuC_6H_4O_7.XH_2O$$

F.W. : 265.51 for X=0, % CU = 23.93
F.W. : 283.53 for X=1, % CU = 22.41
F.W. : 301.54 for X=2, % Cu = 21.07
F.W. : 319.56 for X=3, % Cu = 19.88

The observed copper content of variously dried samples of the solid complex ranged from 20% to 23%. The compound (1:1 solid complex) was extremely soluble in water. A solution as strong as two molar could be made quite easily. Up to a pH of 11.5, there was no effect on the solubility of the compound in water. Beyond this pH, the complex decomposed to a greenishbrown precipitate, probably hydrous copper oxides. The 1:1 solid complex may be used as a stabilizing agent with or without the removal of lithium chloride formed during its preparation.

B. Disodium monocopper(II) citrate (1) Equimolar solutions of copper chloride and sodium citrate were added to water as in A above to obtain a deep blue solution having a pH of about 5. A 50 ml. aliquot of this solution was placed in a separatory funnel. An equal volume of anhydrous acetone was added and the funnel was shaken so as to effect mixing. Upon standing, a two-phase system existed. A blue liquid phase rested on the bottom of the funnel in a reduced volume of approximately 25 ml., while the top layer (approximately 75 ml.) was slightly hazy and colorless, having been crystal clear prior to the shaking process. The blue liquid (oily, viscous) was removed from the funnel through the stopcock and collected in a second separatory funnel. The hazy supernatant was placed in a beaker and evaporated to dryness over a stream bath. An approximate 25 ml. aliquot of anhyrous acetone was added to the second separatory funnel, causing almost instantaneous formation of a plastic-like mass in the bottom of the funnel, as opposed to the oily liquid which had been present there. The supernatant from the plastic mass was placed in a second beaker and labeled supernatant 2. The addition of distilled water to the plastic-like mass resulted in the immediate re-solution of the material. The total volume of the redissolved substance was adjusted to 25 ml., resulting in the formation, once again, of a viscous, oily liquid. Following evaporation to dryness of supernatant 1, microscopic examination of the dry residue revealed the presence of definite, copious amounts of sodium chloride crystals. Evaporation of supernatant 2 yielded a very finely divided powdery residue, containing a small number of distinct sodium chloride crystals. Analysis of the twice-extracted blue oily solution for copper content revealed that the solution contained approximately 125 mg. of copper per milliliter, thereby representing a concentrate of the metal complex which had originally contained approximately 65 mg. per milliliter. The large reduction of the amount of sodium chloride in supernatant 2 indicated that the bulk of the contaiminating by-product salt had been removed. A portion of the concentrate was permitted to evaporate and definitive crystalline material was noted.

(2) The procedures of the preceding paragraph (1) were repeated except that there was a pH adjustment of the initially formed blue solution from about pH 5 to about pH 7 with KOH solution to neutralize the HCl formed. After extraction and evaporation procedures were performed as above, a concentrate of the metal complex was obtained which upon evaporation yielded definite crystalline material.

(3) Equimolar aliquots of copper sulfate and sodium citrate as in paragrapgh (1) were combined followed by pH adjustment of about 7 with NaOH. Procedures of extraction and evaporation of the resulting blue solution as described above yielded an amorphous powder possessing no visually discernible crystalline structure.

The following formula is proposed for the disodium monocopper(II) citrate prepared in paragraphs (1) to (3) above based on the elucidation of the struction and analyses described hereinafter:

$$Na_2CuC_6H_2O_7.XH_2O$$

C. Disodium monozinc citrate

Employing the following ingredients, a zinc complex stabilizer analogous to the copper complex of B above was prepared:

50 ml. cold water
29.4 g. trisodium citrate dihydrate
13.6 g. zinc chloride ($ZnCl_2$)
concentrated HCl
NaOH pellets The $ZnCl_2$ was ground into find particles using a mortar and pestle and then dissolved in the water. The pH was adjusted to between 0.5 and 1.0 with HCl. The sodium citrate was added slowly, with addition of HCl to maintain the pH below 1.0. When all material was dissolved, the solution was neutralized slowly with NaOH pellets. The material remaining in solution at pH 7.2 was decanted, adjusted to a pH of 8.5-9.0 and then extracted with a double volume of a 50:50 methanol acetone solution. The material was collected on a Buchner funnel using Whatman #42 filter paper. Alternatively, the solution can be vacuum dried at 70° C.

D. Disodium mononickel citrate

A nickel complex stabilizer was prepared employing the following ingredients:
- 40 ml. cold water
- 38.4 g. anhydrous citric acid
- 47.5 g. nickel chloride ($NiCl_2$), finely ground
- NaOH flakes The citric acid was dissolved in the water. The nickel salt was added slowly, with constant monitoring of the pH. When all of the material was in solution, NaOH flakes were added slowly (to minimize heat generation) to adjust the pH to between 4.0 and 5.0. The yield was about 100 ml containing about 117 mg/ml $Ni^{++}$.

E. Disodium monomercury citrate

A mercury complex stabilizer was prepared employing the following ingredients:
- 40 ml. water
- 2.2 g. mercuric oxide (HgO)
- 1.9 g. anhydrous citric acid
- NaOH pellets The citric acid was dissolved in water and the solution was warmed to no more than 50° C. The HgO was added slowly, with vigorous stirring, and allowed to react until the solution was clear. The pH was adjusted with NaOH pellets to 8.5-9.0 ensuring that the temperature did not exceed 50° C. The material may be crystallized by either of the methods described for the zinc complex of C above.

DETERMINATION OF METAL COMPLEX DISSOCIATION

The dissociation property of the 1:1 copper citrate complex prepared by the above techniques was determined over a pH range pf 3-12 units using a copper(II) ion specific electrode (Orion CopperII) Specific Electrode). 50 milliliter samples of copper citrate 1:1 solution (0.0068 molar) were adjusted to pH 3, 4, 5, 6, 7, 8, 9, 19, 11 and 12, with the concentration of free copper ion subsequently determined by using the copper ion pecific electrode. The following values of free copper ion concentrations at the indicated pH were obtained and the negative logs of the copper ion concentration letermined.

TABLE

| pH | $Cu^{++}$ | pM |
|---|---|---|
| 3 | $3.2 \times 10^{-3}$ | 2.495 |
| 4 | $9.0 \times 10^{-4}$ | 3.046 |
| 5 | $2.5 \times 10^{-4}$ | 3.602 |
| 6 | $5.3 \times 10^{-5}$ | 4.276 |
| 7 | $1.0 \times 10^{-5}$ | 5.000 |
| 8 | $8.0 \times 10^{-8}$ | 7.097 |
| 9 | $8.8 \times 10^{-12}$ | 11.055 |
| 10 | $9.6 \times 10^{-13}$ | 12.018 |
| 11 | $3.3 \times 10^{-13}$ | 12.482 |
| 12 | $1.34 \times 10^{-13}$ | 12.873 |

From these data, a pM-pH curve was constructed to ndicate the relationship between free $Cu^{++}$ ion concentration and pH as illustrated in the drawing. The drawing is a cartesian coordinate plot (solid black line) of the negative log of the metal ion concentration (pM) versus the negative log of the hydrogen ion concentration (pH) at points listed in the above TABLE. This plot is a sigmoidally shaped curve representative of the proton induced dissociation property of the metal complex. At the pH range of about 9-12, the complex is very stable and the free $Cu^{++}$ concentration is low. At a pH of about 7, the complex is relatively unstable and dissociation into free $Cu^{++}$ is significant, enabling stabilizing function. In the range of between about 7 to about 9 the $Cu^{++}$ is available for controlled release; from about 10% to about 0.1% dissociation of $Cu^{++}$ from the complex occurs. This unexpected dissociation versus pH behavior renders the complexes extremely effective as stabilizing agents for metal working compositions.

In comparison, a Cu EDTA complex curve is represented by the broken line in the drawing as reported by A. Ringbom, "Complexation in Analytical Chemistry", J. Wiley & Sons, N.Y., 1963, p. 360. As illustrated, the pH effect on Cu EDTA complex is represented by a smooth, monotonic curve reaching a limiting effect by proton induced dissociation at about pH 7-9, thereby yielding, for example, only from about 0.001%-0.00001% ionized speices.

Complexes of the ratio one metal:one citrate may have been suggested to exist in dilute solutions in the publication of M. Bobtelsky and J. Jordan, J. Amer. Chem. Soc., Vol. 67 (1945), p. 1824. However, no one has reported the remarkable emulsion stabilizing activities of these derivatives or their abilities to form coordinate structures with emulsified droplets. Moreover, we have also discovered even further unique attributes of such complexes in metalworking fluids as detailed herein.

Further, we have prepared solid metal complexes of the dialkali monocopper(II) citrates and such solid forms are surprisingly unexpected. We have also been able to make high solution concentrations of such metal complexes. The nature of these complexes has definitely been established by using analytical criteria, namely: (1) the mole ratio method introduced by Yoe and Jones (Yoe, J. H. & Jones, A. L.: Ind. Eng. Chem. Anal. Edition, 16; 111, 1944); (2) the method of continuous variation attributed to Job and modified by Vosburgh and Cooper (Vosburg, W. C. & Cooper, G. R.: J. Am. Chem. Soc., 63; 437, 1941); (3) dependence of complex formation on pH and (4) determination of the apparent stability constant of the complex. Spectrophotometric studies, including visible and ultraviolet spectroscopy, pH determinations, as well as infrared spectroscopic measurements were utilized as an additional means of confirmation of our findings on the formation and molecular composition of the 1:1 copper(II) citrate complex.

The 1:1 copper complexes employed here as stabilizing agents are highly soluble indicating that such complexes are ionic in nature. This is further supported by the observation that the color band of solution of the complex migrated toward the anode (positive electrode) in electrophoresis experiments. Visible and UV spectra exhibit 1:1 compound formation. The overall reaction for the complex formation of the (B) structural form appears to be:

$$H^+ + OH^- \rightleftharpoons H_2O \quad \text{(base)} \tag{2}$$

$$K_{abs} = \frac{[\text{Cu-Citrate}^{-2}][H^+]}{[Cu^{+2}][\text{Citrate}^{-3}]}$$

$$K_{eff} = \frac{[\text{Cu-Citrate}^{-2}]}{[Cu^{+2}][\text{Citrate}^{-3}]}$$

Thus, instead of complexing the —COO⁻ groups only, the alcohol, —OH, ionizes and is involved in the coordination. This forms a stable 5-member and probably 6-member ring. Thus, the reaction is drawn to the right (stabilized) by OH⁻ (base) as the product H⁺ is then removed as the reaction proceeds. This results in the very high effective stability constant, $K_{eff}$. The $K_{eff}$ for such a reaction is pH dependent but related to the absolute stability constant, $K_{abs}$ by the relationships.

$$K_{eff} = \frac{[\text{CuCitrate}^-]}{[Cu^{++}][\text{Citrate}^{-3}]}$$

$$K_{abs} = \frac{[\text{CuCitrate}^-][H^+]}{[Cu^{++}][\text{Citrate}^{-3}]}$$

$$K_{abs} = K_{eff} \cdot [H^+]$$

We have found that $K_{abs}$ for the 1:1 complex has a constant value of about $10^{13}$ (a strong complex) over a pH range of about 9–12. The apparent value of $K_{abs}$ drops sharply at pH 7 to 9 and, at pH values less than about 7, there is a further decrease indicating that the complex exists in finite concentrations even at pH 3 to 7.

Metalworking fluid compositions, as explained above, can be formulated from many different types of specific ingredients. See for example the patents mentioned above and "American Society of Tool Engineers - Tool Engineer's Handbook", First Edition, 1953, pp. 357 et sequal, and such disclosures are incorporated herein by reference.

Without limitation, therefore, the following specific examples are illustrative of metalworking fluids and demonstrate the principles of this invention.

EXAMPLE 1

A cutting fluid composition is prepared by mixing the following ingredients on a volume basis.
1% Sodium xylene sulfonate
9% Naphthene sulfonate
90% Mineral oil, approximately 300 vis.

This mixture is then used to prepare a 3% (volume) emulsion by blending with water and the pH is adjusted to about 8.5–8.9 with the addition of HCl. The disodium mono cupric citrate as prepared above is added to the emulsion to provide 100 mg/liter of Cu⁺⁺ in the aqueous phase. When such a metal working fluid is employed in metal cutting operations, it has been found that all the advantages hereto discussed can be achieved.

EXAMPLE 2

A grinding fluid composition is provided employing the same steps as Example 1 with similar results, except 50% naphthene sulfonate, 15% mineral oil (approximately 100 vis.) and 35% tall oil were substituted for the emulsion ingredients.

For the purpose of demonstrating the coordination of metal ions with the emulsified droplets to achieve stabilizing activities according to this invention, the following experiments were performed.

EXPERIMENT 1

Relation of Copper Concentration in the Oil and Water Phases to Percent Oil in the Emulsion and to Initial Metal Complex Concentration METHODS: Emulsions were prepared, to contain 2.5, 5.0 and 10.0% oil in water. Ten ml of each emulsion were pipetted into 16 × 100 ml test tubes. One ml samples of each were removed. Disodium monocupric citrate (hereinafter metal complex) was added to each of these tubes to attain final concentrations of 50, 100 and 150 ppM as Cu⁺⁺. One ml samples were removed immediately after the metal complex and emulsions were mixed. Samples were taken again after 1 hour with occasional mixing during that period.

The oil samples were extracted by adding an equal volume of dichloroethane and 1 drop of saturated KCl, mixing, and spinning for 5 minutes at top speed on the table-top centrifuge. Five-tenths ml of the organic (bottom) layer and 0.1 ml of the aqueous were removed to different test tubes, and 4.9 ml of water was added to the aqueous sample. Two-tenths ml of copper reagent #1 were added to each tube, with mixing and then 0.2 ml of reagent #2 were added. All tubes were mixed well and 5.0 ml of water were added to the tubes containing the organic extract. The tubes containing the organic phase were mixed again and the organic material was allowed to settle to the bottom. Optical densities of the tubes were read at 700 nm against the appropriate blanks (organic or aqueous extract of emulsions with no metal complex added). RESULTS AND CONCLUSIONS: The experimental findings are tabulated below. The percent copper in each phase was determined by correcting the $A_{700}$ for volume differences between the organic and aqueous extracts and adding the $A_{700}$ values for each phase. The "percent total $A_{700}$" of each phase was assumed to be directly related to the percent of total copper in each phase:

| | 50 ppM Metal Complex as Cu⁺⁺ Percent Total Cu⁺⁺ | | | |
|---|---|---|---|---|
| | Organic Phase | | Aqueous Phase | |
| % Oil | $T_0$ | $T_{60}$ | $T_0$ | $T_{60}$ |
| 2.5 | 0.9 | 0.0 | 99.1 | 100.0 |
| 5.0 | 13.0 | 22.7 | 87.0 | 77.3 |
| 10.0 | 19.2 | 25.9 | 80.8 | 74.1 |

| | 100 ppM Metal Complex as Cu⁺⁺ Percent Total Cu⁺⁺ | | | |
|---|---|---|---|---|
| | Organic Phase | | Aqueous Phase | |
| % Oil | $T_0$ | $T_{60}$ | $T_0$ | $T_{60}$ |
| 2.5 | 0.8 | 3.6 | 99.2 | 96.4 |
| 5.0 | 10.6 | 12.2 | 89.4 | 87.8 |
| 10.0 | 12.7 | 13.6 | 87.3 | 86.4 |

| | 150 ppM Metal Complex as Cu⁺⁺ Percent Total Cu⁺⁺ | | | |
|---|---|---|---|---|
| | Organic Phase | | Aqueous Phase | |
| % Oil | $T_0$ | $T_{60}$ | $T_0$ | $T_{60}$ |
| 2.5 | 1.0 | 1.0 | 99.0 | 99.0 |
| 5.0 | 8.4 | 11.7 | 91.6 | 88.3 |
| 10.0 | 11.9 | 12.6 | 88.1 | 87.4 |

The results showed clearly that at any one metal complex concentration the percent total copper in the organic phase increased slowly with time. This effect was most marked in the samples containing 5.0% oil in the emulsion. The adsorption of Cu⁺⁺ into the oil layer appears to be, in enzymologic terminology, first order with respect to concentration of both oil and metal complex, with the concentration of copper in the oil leveling off at the saturation point of the oil. A Michaelis-Menten curve is expected for rate of transfer of $Cu^{++}$ into the oil phase, as is discussed below.

At a given time and metal complex concentration, the percent total copper in the organic phase was directly related to the percent oil in the emulsion. The correlation was most obvious in the 50 ppM metal complex samples. The amount of copper in the organic phase was dependent on the concentration of oil in the sample, indicating that copper was binding or coordinating directly to the surface of the oil particles.

As the metal complex concentration was increased, an equivalent increase in percent $Cu^{++}$ in the organic phase was not seen. This phenomenon suggests several different mechanisms of $Cu^{++}$ transfer into the oil. The size of oil particles in the emulsion is certainly not uniform. Therefore, the total oil particle surface area in the 10.0% oil emulsion was not 4 times as great as that in the 2.5% oil emulsion. The variation in particle size affects the amount of copper that can be transferred inot the organic layer. An equilibrium may exist between copper in the oil and water phases. The 'equilibrium constants' for transfer in both directions may be determined by concentrations of metal complex in the aqueous phase, i.e., the reactant concentration, and concentrations of organic copper and citrate salts. The transfer of metal complex can be described as follows:

Where $X^{+++}$ is any simple or complex cation carrying 3 positive charges; $\kappa_1$ is determined by the dissociation constant of metal complex at pH 9, and $\kappa_3$ by the rate of adsorption of copper into the oil phase and the affinity of citrate and di- and tri-valent cations for each other. Evidently, $\kappa_1 > \kappa_2$ and $\kappa_3 > \kappa_4$, since with greatly increased time and shearing, virtually all copper has been found in the organic phase. The notions of an equilibrium relationship and time dependence for adsorption correlate well with Michaelis-Menten-like curves.

EXPERIMENT 2

Relation of Copper Concentration in the Oil and Water Phases to Shearing of Oil Particles METHODS. A 50% oil concentrate was sheared by passing three times through a homogenizer at 8000 p.s.i. The oil particles were found to be under $0.1\mu m$ in diameter. The same concentrate, unhomogenized, was found to have a wide range of oil particle size, $0.8-3\mu m$, with the average diameter approximately $1.5\mu m$.

The two concentrates were mixed with tap water to obtain 10% oil in water emulsions, since this percent oil emulsion was shown in the previous experiment to yield the greatest rate of adsorption of $Cu^{++}$ into the oil phase. A 2 ml sample of each emulsion ws taken and centrifuged to remove any gross particulate matter. Metal complex was added to each emulsion to yield 100 ppM as $Cu^{++}$ and 2 ml samples were removed and centrifuged immediately. One ml aliquots of the supernatants were extracted and assayed as described in EXPERIMENT 1. The emulsions were shaken gently for 1 hour and 2 ml samples were removed and treated as described above after 10, 30, and 60 minutes.

RESULTS: The experimental findings are tabulated below. The percent copper in each phase was determined as described in EXPERIMENT 1.

TABLE 2:

Percent Total Copper in each Phase as a Function of Time and Homogenization.

| Time (min.) | Percent Total $Cu^{++}$ (100 ppM Metal Complex Added) | | | |
|---|---|---|---|---|
| | Organic Phase | | Aqueous Phase | |
| | Homogenized | Unhomogenized | Homogenized | Unhomogenized |
| 0 | 13.5 | 11.3 | 86.5 | 88.7 |
| 10 | 18.3 | 20.3 | 81.7 | 79.7 |
| 30 | 25.3 | 14.9 | 74.7 | 85.1 |
| 60 | 27.0 | 18.1 | 73.0 | 81.9 |

A comparison of these results with those from EXPERIMENT 1 showed that considerably more copper had been adsorbed into the organic phase of the homogenized material and somewhat more into the organic phase of the unhomogenized material. If the concentration of metal complex added to these samples, particularly to the homogenized material, had been increased, a higher copper level in the organic layer would be expected. In a circulating metalworking coolant with hgih concentrations of divalent cations, such as $Mg^{++}$ and $Ca^{++}$, present to compete for the citrate moiety, the reaction rate for copper adsorption ($\kappa_1$ and $\kappa_3$) should be greater.

The results of this experiment demonstrate quite well the validity of a Michaelis-Menten analysis of the copper adsortion rate. The greatest rate of uptake of copper into the organic phase of the homogenized sample ocurs in the first 10 minutes after metal complex has been added to the coolant. From 10 to 60 minutes a lower copper adsorption rate is noted. More copper has been taken up by the homogenized rather than unhomogenized oil particles. A far higher initial rate of copper adsorption is seen in the homogenized oil sample, due to the enormous surface area of the oil particles. These effects verify that copper adsorption to oil is also a surface phenomenon, i.e., that the copper binds to the surface of the oil particles rather than becoming incorporated into them.

In view of the above detailed description, it will be apparent that other modifications of these inventions may be made without departing from the spirit and scope thereof.

What is claimed is:

1. A stabilized metalworking fluid composition comprising
   an oil and water dispersion,
   an emulsifying agent selected from the group of anionic and nonionic agents, and mixtures thereof, which imparts an electronegativity to the oil phase of the dispersion and, as a stabilizer therefor in an effective stabilizing amount,
   a multivalent metal ion bonded to said electronegative oil phase to impart stability to the dispersion.

2. The composition of claim 1 wherein the effective amount of metal ion is in the range of about 10 to about 500 mg/liter of the oil phase.

3. A stabilized metalworking fluid composition comprising an oil and water dispersion and, an emulsifying agent selected from the group of anionic and nonionic agents, and mixtures thereof, which imparts an electronegativity to the oil phase of the dispersion, and as a stabilizer therefor in an effective stabilizing amount, a metal complex of a heavy metal ion and a polyfunctional organic ligand, in a ratio of 1:1 of the metal ion to the ligand, said ligand selected from the group of an organic acid and a substituted organic acid, said complex having an aqueous proton induced dissociation property represented by a sigmoidally shaped curve on a cartesian coordinate plot of the megative log of the metal ion concentration versus the negative log of hydrogen ion concentration, said dissociation property causing the controlled release of metal ion to impart stability to the dispersion.

4. The composition of claim 3 having an alkaline pH up to about 12.

5. The composition of claim 3 having an alkaline pH within the range of about 7 to about 9.

6. The composition of claim 3 wherein the controlled release of metal ion is such that from about 10% to about 0.1% of said metal ion in said complex is released over a pH range of about 7 to about 9.

7. The composition of claim 3 wherein said metal complex is a complex of a divalent metal ion and a polyfunctional organic ligand in a ratio of 1:1, respectively.

8. The composition of claim 7 wherein said metal is selected from the group consisting of copper, nickel and mercury and said ligand is citric acid.

9. The composition of claim 7 wherein said organic ligand is an alpha-hydroxy polycarboxylic acid.

10. The composition of claim 3 wherein said metal complex is a dialkalimetal monocopper(II) citrate.

11. The composition of claim 3 wherein said metal complex is contained in an amount providing about 10 mg to about 500 mg of ion per liter of aqueous phase.

12. A method of stabilizing a metalworking fluid composition of an oil and water dispersion comprising the steps of preparing a dispersion of oil and water with an emulsifying agent selected from the group of anionic and nonionic agents, and mixtures thereof, which imparts an electronegativity to the oil phase and providing in the aqueous phase of said composition an effective stabilizing amount of a multivalent metal ion for bonding to said electronegtaive oil phase to impart stability to the dispersion.

13. A method of claim 12 wherein said metal ion is introduced in the aqueous phase as a metal complex of a heavy metal ion and a polyfunctional organic ligand, in a ratio of 1:1 of the metal ion to the ligand, said ligand selected from the group of an organic acid and a substituted organic acid, said complex having an aqueous proton induced dissociation property represented by a sigmoidally shaped curve on a cartesain coordinate plot of the negative log of the metal ion concentration versus the negative log of the hydrogen ion concentration, said dissociation property causing the controlled release of the metal ion to impart stability to the dispersion.

14. The method of claim 13 wherein said dispersion is first prepared and said metal complex is introduced into the aqueous phase of said dispersion.

15. The method of claim 13 wherein said metal complex is introduced into the aqueous phase of the composition prior to the preparation of said dispersion.

16. The method of claim 13 wherein said dispersion has an alkaline pH below about 12.

17. The method of claim 13 wherein said dispersion has an alkaline pH within the range of about 7 to about 9.

18. The method of claim 13 wherein said complex is a dialkalimetal monoheavymetal chelate of an alpha-hydroxy polycarboxylic acid.

19. The method of claim 18 wherein said chelate is dialkalimetal monocopper(II) citrate.

20. The method of claim 19 whrein said chelate is provided in aqueous admixture.

21. The method of claim 19 wherein about 10 to about 100 mg copper metal ion per liter is introduced into the aqueous phase.

22. The method of claim 21 including maintaining said amount in the aqueous phase of said composition during its use in metalworking operations.

23. A method of stabilizing a metalworking fluid composition comprising a dispersion of oil and water with an emulsifying agent selected from the group of anionic and nonionic agents by providing in the aqueous phase a dialkalimetal monocopper(II) citrate in an amount of about 10 mg to about 500 mg of copper ions per liter of aqueous phase at an alkaline pH within the range of about 7 to about 9.

24. The stabilized composition of claim 23.

* * * * *